United States Patent [19]

Betz

[11] Patent Number: 4,617,013

[45] Date of Patent: Oct. 14, 1986

[54] METHOD AND APPARATUS FOR SURGICAL IRRIGATION, ASPIRATION AND ILLUMINATION

[75] Inventor: John J. E. Betz, Reno, Nev.

[73] Assignee: Timron Instruments, Incorporated, San Diego, Calif.

[21] Appl. No.: 689,511

[22] Filed: Jan. 8, 1985

Related U.S. Application Data

[63] Continuation of Ser. No. 475,042, Mar. 14, 1983, abandoned.

[51] Int. Cl.[4] .............................................. A61M 7/00
[52] U.S. Cl. .......................................... 604/39; 128/6; 604/902
[58] Field of Search ................... 128/4, 6; 604/19-21, 604/35, 36, 49, 50, 39, 43, 131, 54, 73, 902

[56] References Cited

U.S. PATENT DOCUMENTS

| Re. 17,319 | 6/1929 | Parkler | 604/39 |
|---|---|---|---|
| 2,812,765 | 11/1957 | Tofflemire | 604/35 |
| 3,071,129 | 1/1963 | Wasserman | 128/6 |
| 3,089,484 | 5/1963 | Hett | 128/6 |
| 3,191,600 | 6/1965 | Everett | 604/902 |
| 3,261,356 | 7/1966 | Wallace | 128/6 X |
| 3,850,162 | 11/1974 | Iglesias | 128/6 |
| 3,945,375 | 3/1976 | Banko | 128/6 |
| 4,149,315 | 4/1979 | Page, Jr. et al. | 604/131 |
| 4,204,328 | 5/1980 | Kutner | 604/902 |

Primary Examiner—John D. Yasko
Attorney, Agent, or Firm—Freilich, Hornbaker, Rosen & Fernandez

[57] ABSTRACT

This invention is a method and an apparatus for surgical irrigation, aspiration and illumination comprising a cooperative irrigation, aspiration and illumination system wherein the three functions are cooperatively performed at the actual surgical area during surgery. A single hand-held instrument capable of simultaneously and cooperatively providing light, irrigation and aspiration in a single and simultaneous act is utilized in a preferred method of practicing this invention. The light flows around the aspiration tip, which in turn carries the irrigation member. The amount of irrigation and aspiration is controlled by a one-hand operation of the surgeon or other operating room attendant.

21 Claims, 6 Drawing Figures

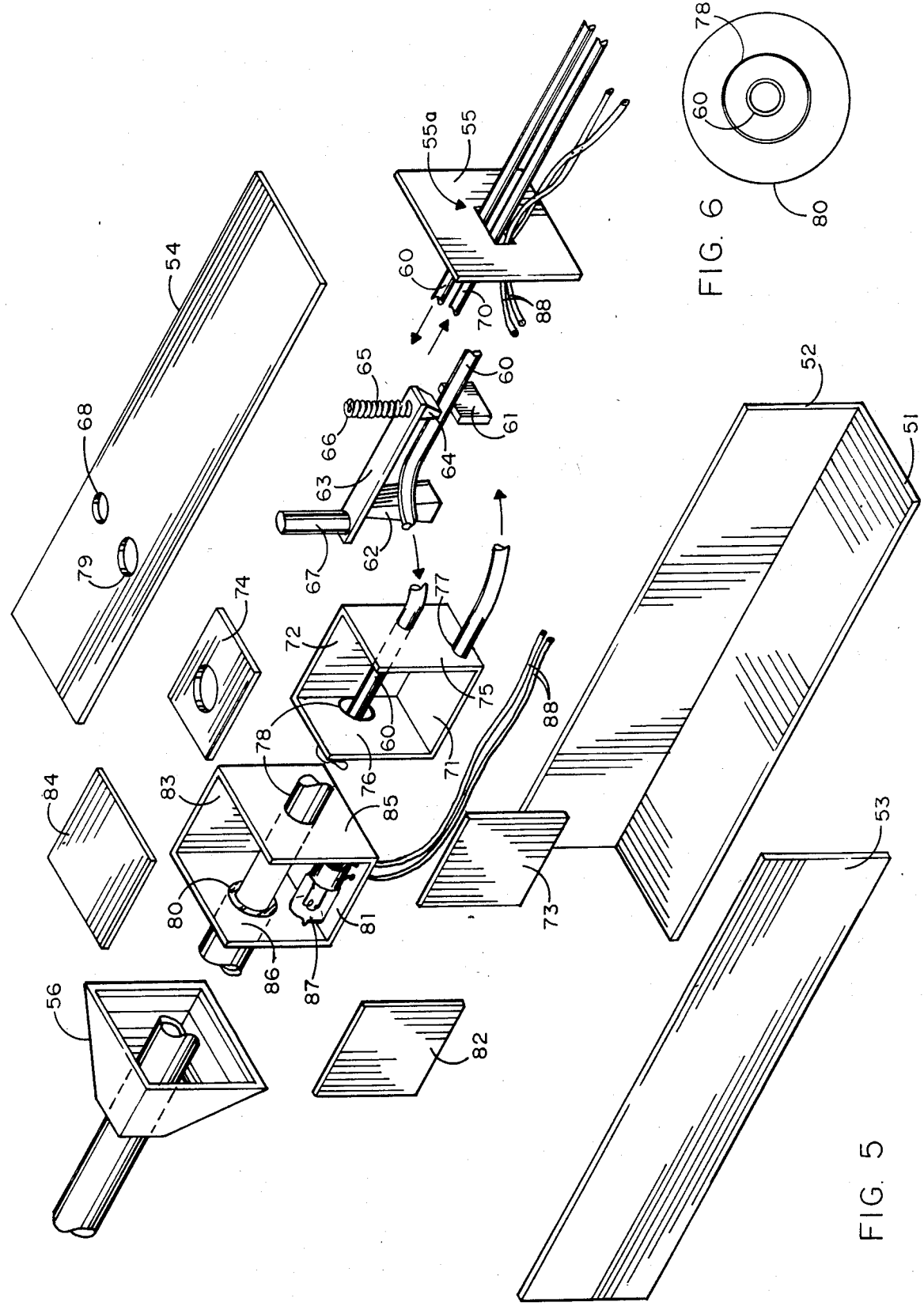

METHOD AND APPARATUS FOR SURGICAL IRRIGATION, ASPIRATION AND ILLUMINATION

CROSS REFERENCE TO RELATED PATENT APPLICATIONS

This application is unrelated to any other patent application filed by me, except for Design Patent Application being filed simultaneously herewith for design of SURGICAL IRRIGATION, ASPIRATION AND ILLUMINATION INSTRUMENT. Also this application is a continuation of Ser. No. 475,042, filed Mar. 14, 1983, now abandoned.

BACKGROUND OF THE INVENTION

1. Field of the Invention

This invention is in the general field of surgical procedures and instruments. It is more particularly directed to a surgical procedure and instrument combining illumination of a surgical area with cooperative irrigation and aspiration. It is even more specifically directed to the cooperative and simultaneous irrigation, aspiration and illumination of the surgical area by one hand-held instrument operated with one hand by a surgeon or assistant.

2. Description of the Prior Art

All prior art in the field concerned comprises independent lighting sources (usually overhead lights), hand operated aspiration tubes and syringes, and independent irrigation tubes. In one instance there has been an attempt to combine the irrigation and aspiration functions in one instrument. There has been no art wherein the illumination can or has been brought in for purposes of improved observation and exposure and visibility. Such prior art will be described in more detail in the description of the prior art and in the summary which follow.

In effect there is no prior art as to the present invention. This is the first time a method and instrument for performing the method has been conceived wherein one person can simultaneously perform the three functions (irrigation, aspiration and illumination) with a single, one hand, instrument.

SUMMARY OF THE INVENTION

In many surgical procedures (for example and without limitation, vascular surgery, oral surgery, and the like) it is most important (and difficult) to provide adequate lighting at the surgical site. Until my invention it has been customary to provide large overhead lights in surgical rooms. On occasion some surgeons or assistants may carry auxilliary lights of one type or another to attempt to improve lighting at the exact position of surgery. In this type of lighting, shadows and the like are a problem due to interference with the light path by the persons and instruments and equipment being used.

Another important function during many surgical procedures is the irrigation of the surgical area with various fluids. It has been customary until now to use hand-held syringes, filled by a nurse or other surgical assistant, and to irrigate by squeezing the syringe bulb. This has many problems including, among others, the necessity for a surgical assistant to spend much time filling the syringes, delay in irrigating when desired, inaccurate pressure control of the irrigation fluid, and the like.

Still one more critical surgical function is the function of aspiration of fluids, small particles of material, and the like from the surgical area. In this function an aspiration tube is handled by one of the surgical team and the various materials are drawn by suction into the tube and away from the surgical area by a vacuum through the aspiration tube. It is extremely important that this function be performed effectively.

The three functions, irrigation, aspiration and illumination, when performed independently (as they always have until my invention) can actually interfere with one another and cause delays in the surgery.

I have studied this problem and have now conceived and developed a new and improved method (and apparatus) for the cooperative, simultaneous and combined performing of the three surgical functions of irrigation, aspiration and illumination of surgical areas. At the same time, my method allows for independent operation of the functions for periods of time if desired without interference with the surgical procedures or operation of the other functions.

I have been able to achieve the much desired and sought after result of greatly increased exposure and visibility of the area of the operation by the combination of these three functions of irrigation, aspiration, and illumination, all directed precisely to the area where such visibility and exposure is most necessary and is usually most lacking.

In perfecting this invention I have developed a small single hand-held instrument through which lighting is provided to an instrument tip by means of a light channel which can take many forms, such as glass fiber optics, light conducting plastics, and the like. Cooperative with the light directing source is an aspiration tip connected to an aspiration device. Further, an irrigation tip is provided cooperative with the light source and aspiration tip so that the three functions all operate through the one instrument and without interference with each other as the functions are activated during surgery at the actual site of the surgery. The aspiration is controlled by a one-finger control (preferably a bleed hole for the vacuum). The irrigation is controlled through the same instrument by means of a simple pinch valve or the like to the irrigation line which is under a constant controlled pressure. The illumination is normally constant, playing about the aspiration and irrigation points.

It is an object of this invention to provide improved illumination at the point of surgery during surgical procedures.

Another object of this invention is to provide for controlled and cooperative irrigation and aspiration in connection with the improved source of illumination at the surgical site.

Another object of this invention is to eliminate the delays and wasted time of surgical personnel in performing the irrigation and aspiration functions, at the same time maintaining superior illumination at the surgical site.

The foregoing and other objects and advantages of this invention will become apparent to those skilled in the art upon reading the description of a preferred embodiment in conjunction with a review of the appended drawings.

BRIEF DESCRIPTION OF THE DRAWINGS

FIG. 5 is an enlarged, exploded, schematic perspective of the instrument used in FIG. 4 with certain portions broken away; and FIG. 6 is an enlarged end-view of the instrument tip used in FIG. 4.

DESCRIPTION OF A PREFERRED EMBODIMENT

Figure 1:
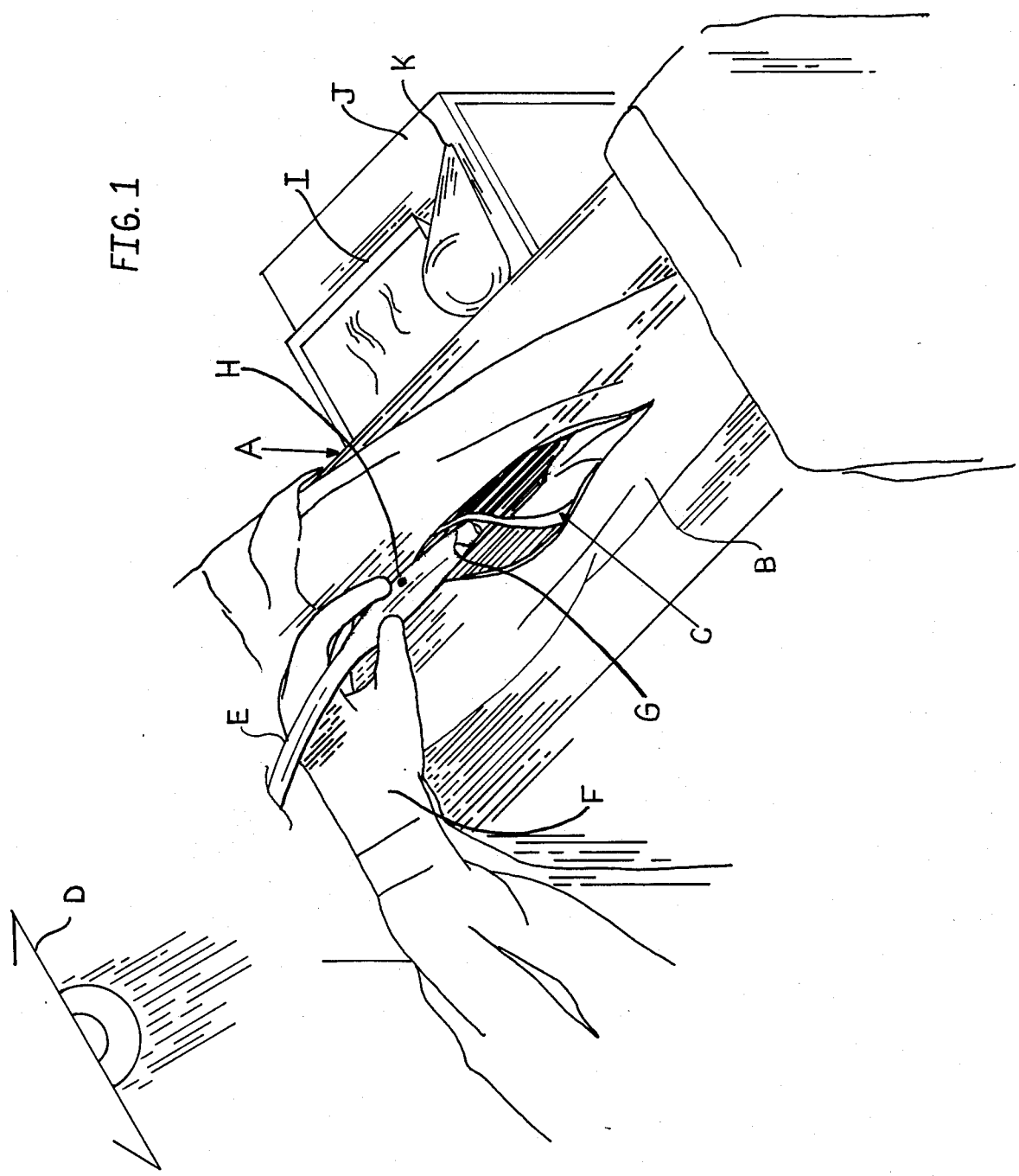
FIG. 1 is a schematic perspective illustrating the manner in which the functions of this invention have heretofore been performed.

FIG. 1 illustrates the manner in which the lighting, irrigation and aspiration functions have heretofore been accomplished in surgical procedures. In this case, a leg B of a patient is undergoing surgery. The leg is on an operating table or the like A. The area of surgery is indicated by the general reference C. A customary overhead lighting arrangement is shown at D. A member of the operating team is holding an aspiration tube # with his hand F. The aspiration tip G is shown in the surgical area. A bleed hole H is used to control the aspiration.

Table, or stand, J holds a bowl I which will contain the irrigation fluid. A syringe K is shown on the table J. When it is desired to irrigate the surgical area it will be necessary for the person handling the aspiration to put it aside to fill the syringe, or someone else must fill the syringe K.

The hand F and the aspiration tube E and tip G will normally cast shadows or obscure the light from light D.

Figure 2:
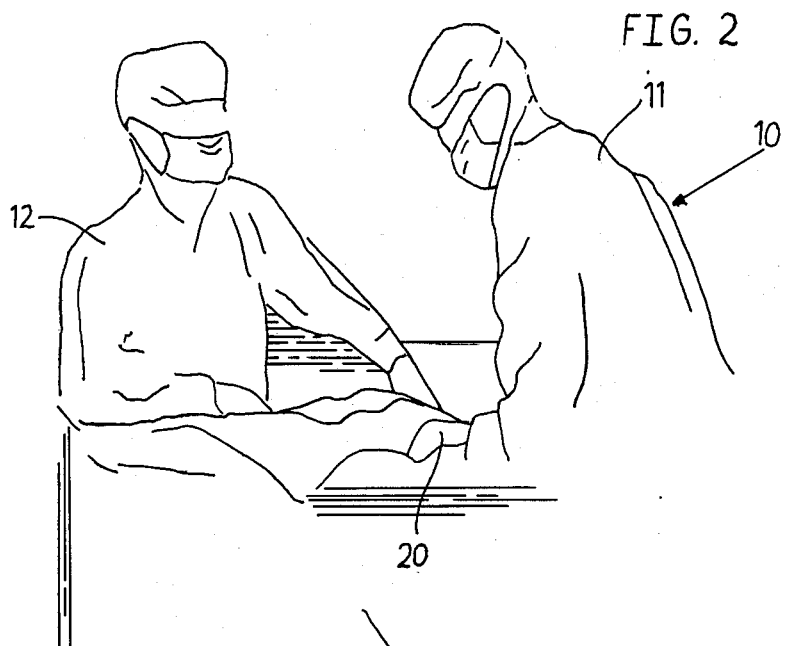
FIG. 2 is a schematic perspective of an operating area scene.

FIG. 2 illustrates an operating scene generally 10 with a surgeon 12 and assistant 11 performing surgery on a patient's leg 20.

Figure 3:
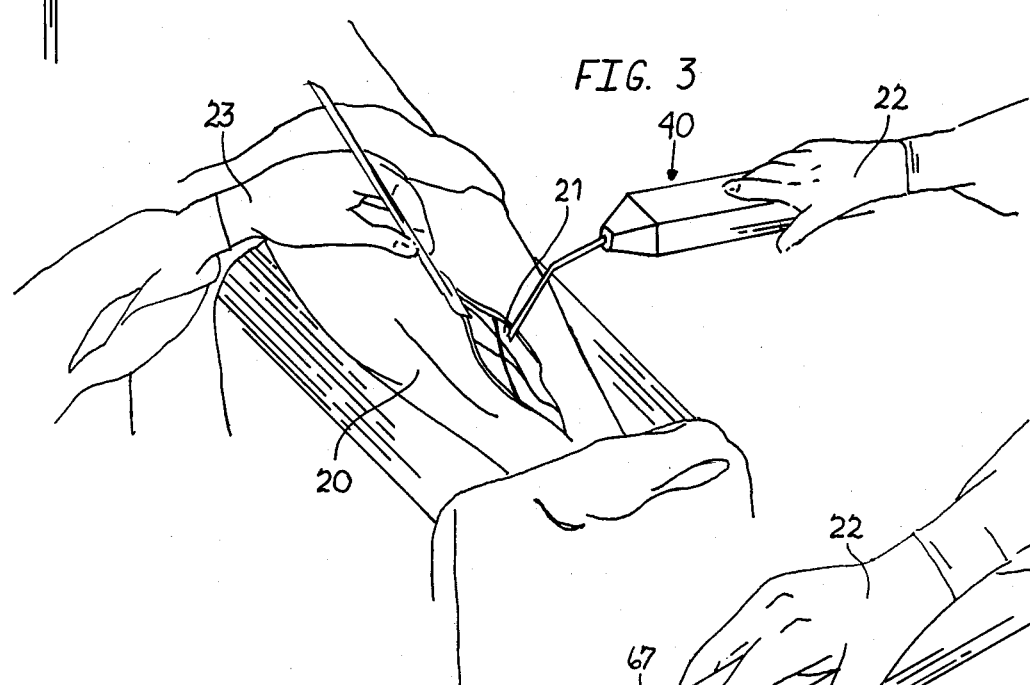
FIG. 3 is an enlarged schematic perspective of a portion of the area of FIG. 2 from a different angle and with certain elements illustrating the practice of this invention shown and with other elements from FIG. 2 eliminated.

FIG. 3 shows the leg 20 from FIG. 2 somewhat enlarged and from a different angle to show the surgical area 21, the surgeon's hand 23, and the assistant's hand 22 holding a preferred instrument 40 used in the practice of this invention.

Figure 4:
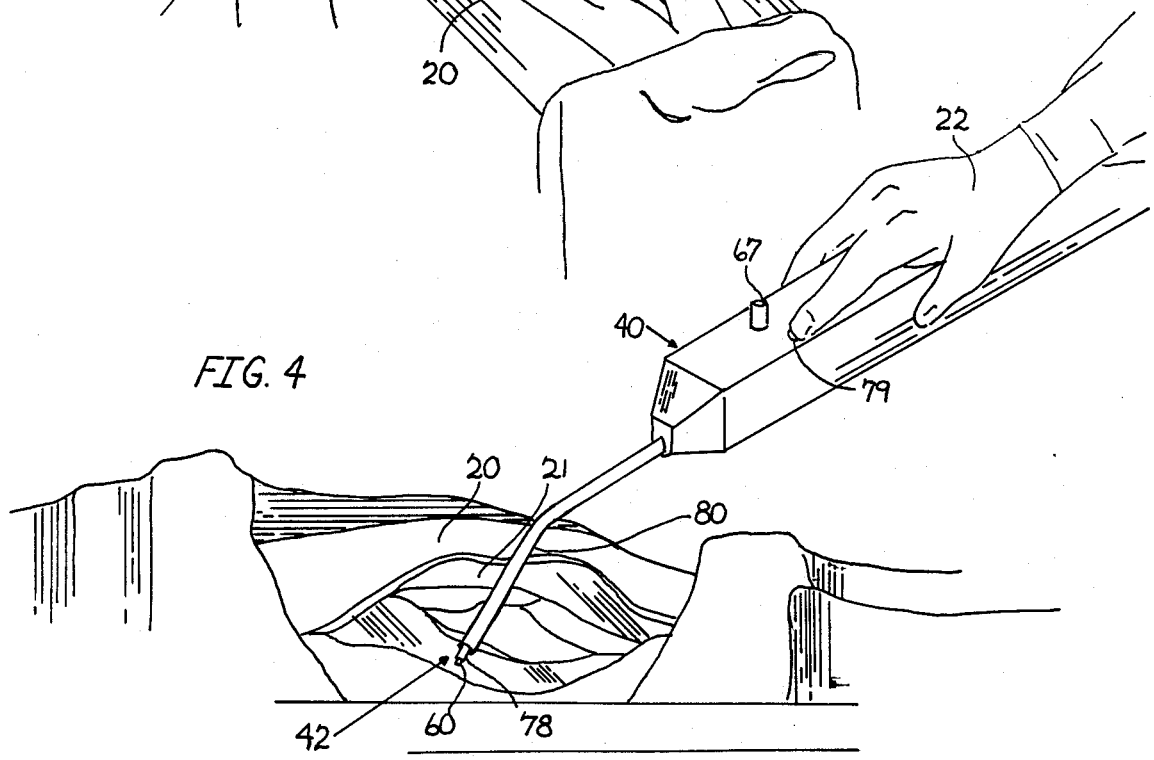
FIG. 4 is an enlarged schematic perspective of a portion of FIG. 3 from a very slightly different angle.

FIG. 4 depicts the scene of FIG. 3 enlarged and from a slightly different angle. Here, the surgical area 21 of the leg 20 is shown with the tip 42 of the instrument 40 in close proximity. The irrigation tip and tube 60 is shown within the aspiration tube 78, which is enclosed within the light conducting and emitting material 80. The hand 22 of the assistant is holding the instrument 40. One finger may be used to control the aspiration rate by covering, or partially covering, bleed hole 79. Another finger may be used as desired to control the irrigation flow through activation as is explained below of the irrigation control button 67.

It must be carefully observed that the assistant holding this instrument will be directing the light from light transmission material 80 directly in the area of the surgery, at the same time controlling the irrigation and aspiration from the exact surgical area. In this manner the surgeon has optimum lighting and the irrigation and aspiration is controlled in exactly the proper manner. There are no delays due to filling syringes or the like.

FIG. 5 shows the parts of the preferred instrument to practice the method of this invention in exploded view. The instrument is basically contained within a rectangular housing composed of four pieces 51, 52, 53 and 54 glued, or otherwise fastened, together or even formed in one piece. The rear end piece 55 will be appropriately glued or otherwise fastened to the ends of the elements forming the basic housing. The end 55 has an opening 55a through which the tubes and the like hereinafter described will pass. The front of the instrument comprises a nose piece 56 through which the light transmitting element 80 will pass. Within the light transmitting element will be the aspiration tube 78, carrying within it the irrigation tube 60.

The nose piece could be formed in one piece and glued or otherwise fastened to the basic housing or can be formed from various pieces as somewhat indicated in FIG. 5 and then assembled by gluing or the like. It will be observed that the irrigation tube 60 is mounted over a block 61 within the housing. A wedger-shaped element 64 is fastened to a rocker arm 63 which pivots upon a fulcrum 62. Spring 66, mounted or otherwise affixed appropriately to an appendage 65 on the rocker arm 63 will press up against the top of the housing 54 to tend to maintain the wedge element 64 in a position where it pinches tube 60 so the irrigation fluid does not flow. The rod 67, which is attached to rocker arm 63, extends above the top of the housing element 54 through hole 68. By pressing down upon the rod 67 the wedge element 64 is lifted and the irrigating fluid will flow depending upon how much it is lifted.

The aspiration line 70 enters into a box-like element 71, 72, 73, 74, 75 and 76. These elements are glued together and have a completely tight fit at all areas including the hole through which irrigation line 60 enters the box. Line 60 exits the box within a second aspiration line 78. Thus this box becomes a suction chamber. The hole 79 in housing element 54 fits identically with the hole in element 74 of the suction box and element 74 is firmly adhered to the housing element 54 so as to make a tight seal. The amount of suction is controlled by placing a finger over the hole at 79 or partially or completely removing it.

The suction line 78 together with the irrigation line 60 carried inside next enters a light chamber formed of the elements 81, 82, 83, 84, 85 and 86, which are glued, or otherwise fastened, together. Preferably the interior surface of these elements will be reflectorized. A light 87 mounted in a socket of normal construction and activated through wires 88 will be mounted within the box to provide light. The aspiration line 78 carrying the irrigation line 60 enters into light conducting element 80 as shown. This light conducting element may be of a plastic material which conducts light along its length, such as polyethylene, polyester, or the like. Also this could be formed of glass fibers. Thus, the light will be surrounding the irrigation tube and the aspiration tube and at its exit position the light will then emanate from the light conducting material 80 around the aspiration and irrgation tubes and provide light to the actual surgical area. This results in greatly improved visibility and exposure of the area being treated so that the surgeon has the maximum ability to see and properly the area in which he is actually working.

FIG. 6 illustrates in greatly enlarged form the end, as an end view, of the instrument without a showing of the background elements looking from the end into the instrument. It will be seen that irrigation tube 60 is surrounded by the aspiration tube 78 which in turn is surrounded by the light emitting material 80.

In use, the operator of this instrument will be able to hold the instrument and use one or two fingers to control the bleed hole 79 and the irrigation activator 67. They can be intermittently or jointly activated or deactivated as may be desired.

While the embodiment of this invention shown and described is fully capable of achieving the results desired, it is to be understood that this embodiment has been shown and described for purposes of illustration only and not for purposes of limitation.

I claim:

1. A device for probing a surgical incision which can be held in and operated by one hand and which is adapted to provide light and irrigating fluid to a surgical incision and to aspirate fluid therefrom comprising:
   a. an elongated probe member having at or near the distal end thereof
      i. a vacuum means for aspirating fluids from the surgical incision,
      ii. a fluid supply means for providing irrigating fluid to the surgical incision, and
      iii. a light means to illuminate the surgical incision; and
   b. a housing member connected to the proximal end of the probe member capable of being held in the hand and provided with control means which can be operated by the hand holding the device during the use thereof, said housing having
      i. a conduit means in fluid communication between a vacuum source and the vacuum means in the probe member, and
      ii. a conduit means in fluid communication between a fluid source and the fluid supply means in the probe member;
   said probe member being hollow and wherein said light means includes an annular light conducting element disposed in said probe member; and wherein
   said vacuum means includes a first tube disposed in said probe member within said annular light conducting element for providing a vacuum at the distal end of said probe member; and wherein
   said fluid supply means includes a second tube disposed in said probe member within said annular light conducting element for supplying irrigating fluid at the distal end of said probe member.

2. The device of claim 1 wherein the control means includes:
   means to control the vacuum provided by said first tube at the distal end of said probe member.

3. The device of claim 1 wherein the control means includes:
   means to control the flow of irrigating fluid supplied by said second tube at the distal end of said probe member.

4. The probe device of claim 1 wherein said second tube is disposed within the first tube.

5. The probe device of claim 1 wherein the probe member is provided with an opening at or near the distal end thereof in communication with said first tube providing a vacuum.

6. The probe device of claim 5, wherein the probe member is provided with an opening at or near the distal end thereof in communication with said second tube providing irrigation fluid.

7. The probe device of claim 1, wherein the probe member has an opening at or near the distal end thereof in communication with said light conducting element to illuminate the surgical incision.

8. The probe device of claim 1, wherein the conduit means in fluid communication between the fluid source and the fluid supply means is a flexible tube.

9. The probe device of claim 8, wherein said control means includes a finger operated means to control the flow of irrigating fluid from the source thereof to the fluid supply means comprising a pincher valve which operates on the flexible tube.

10. The probe device of claim 1, wherein the conduit means in fluid communication between the vacuum source and the vacuum means in the probe member is provided with a bleed hole to control the level of vacuum.

11. The probe device of claim 1 including a light source mounted in said housing member optically connected to said light conducting element to transmit light from the light source to the distal end of the probe member.

12. A surgical instrument for enabling a user using one hand to probe an incision and illuminate, irrigate and/or aspirate said incision, said device comprising:
   an elongated handle member having first and second ends and a perimeter wall defining a cross section dimensioned so as to fit comfortably in said user's one hand;
   an elongated probe member having first and second ends, said probe member first end attached to said handle member second end;
   irrigation passageway means formed in said handle member and probe member extending from said handle member first end to said probe member second end for conveying a first fluid from a fluid supply coupled to said handle member first end for discharge at said probe member second end;
   aspiration passageway means in said handle member and probe member extending from said handle member first end to said probe member second end for drawing a second fluid from said probe member second end to a vacuum source coupled to said handle member first end;
   illumination passageway means in said probe member for conducting light from said probe member first end to said probe member second end;
   first control means carried by said handle member responsive to finger pressure applied substantially perpendicular to the elongation of said handle member for controlling the flow of said first fluid through said irrigation passageway means;
   second control means carried by said handle member responsive to finger pressure applied substantially perpendicular to the elongation of said handle member for controlling the flow of said second fluid through said aspiration passageway means, said first and second control means being located in close proximity to one another on said handle member whereby said user can readily apply pressure to said first or second control means using a single finger of said user's one hand; and
   means carried by said handle member for supplying light proximate to said illumination passageway means at said probe member first end.

13. The device of claim 12 wherein said illumination passageway means comprises an elongated rod of light conducting material; and wherein said means for supplying light comprises an electrically energizable light source mounted within said peripheral wall of said handle member.

14. The device of claim 12 wherein said first control means includes a normally closed valve mounted in said handle member and a valve actuator member extending through said handle member perimeter wall and mounted for reciprocal movement substantially perpendicular to said handle member elongation whereby said user can apply finger pressure thereto to open said normally closed valve.

15. The device of claim 12 wherein said elongated probe member has a perimeter wall defining a cross section smaller than said handle member cross section.

16. The device of claim 12 wherein said
second control means includes an air hole formed in said handle member whereby a user can apply finger pressure thereto for increasing the flow of said second fluid through said aspiration passageway means.

17. A surgical instrument for enabling a user using one hand to probe an incision and simultaneously illuminate, irrigate and aspirate said incision, said device comprising:
an elongated handle member having first and second ends and a perimeter wall defining a cross section dimensioned so as to fit comfortably in said user's one hand;
an elongated probe member having first and second ends, said probe member first end attached to said handle member second end;
irrigation passageway means formed in said handle member and probe member extending from said handle member first end to said probe member second end for conveying a first fluid from a fluid supply coupled to said handle member first end for discharge at said probe member second end;
aspiration passageway means in said handle member and probe member extending from said handle member first end to said probe member second end for drawing a second fluid from said probe member second end to a vacuum source coupled to said handle member first end;
illumination passageway means in said probe member for conducting light from said probe member first end to said probe member second end;
first control means carried by said handle member and operable by a single finger of said users one hand for controlling the flow of said first fluid through said irrigation passageway means; and
electrically energizable light source means mounted within said peripheral wall of said handle member for supplying light proximate to said illumination passageway means at said probe member first end.

18. The device of claim 17 wherein said light source means is mounted in close proximity to said aspiration passageway means whereby said second fluid drawn therethrough can carry away heat produced by said light source means.

19. The device of claim 18 further including:
second control means carried by said handle member and operable by a single finger of said users one hand for controlling the flow of said second fluid through said aspiration passageway means.

20. The device of claim 19 wherein said first and second control means are located in close proximity to one another on said handle member whereby said first and second control means can be operated using the same single finger of said user's one hand.

21. The device of claim 20 wherein each of said first and second control means is responsive to finger pressure applied substantially perpendicular to the elongation of said handle member.

* * * * *